United States Patent
Hawkins (10) Patent No.: US 11,583,225 B2
(45) Date of Patent: *Feb. 21, 2023

(54) DIAGNOSTIC KNEE ARTHROMETER FOR DETECTING ACL STRUCTURAL CHANGES

(71) Applicant: THE REGENTS OF THE UNIVERSITY OF CALIFORNIA, Oakland, CA (US)

(72) Inventor: David Hawkins, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 957 days.

This patent is subject to a terminal disclaimer.

(21) Appl. No.: 16/409,268

(22) Filed: May 10, 2019

(65) Prior Publication Data

US 2019/0357841 A1     Nov. 28, 2019

Related U.S. Application Data

(63) Continuation of application No. 15/177,033, filed on Jun. 8, 2016, now Pat. No. 10,327,694, which is a
(Continued)

(51) Int. Cl.
*A61B 5/00*      (2006.01)
*A61B 5/11*      (2006.01)
(Continued)

(52) U.S. Cl.
CPC .......... *A61B 5/4585* (2013.01); *A61B 5/1121* (2013.01); *A61B 5/1126* (2013.01); *A61B 5/296* (2021.01); *A61B 5/702* (2013.01); *A61B 5/389* (2021.01); *A61B 2562/0261* (2013.01); *A61B 2562/06* (2013.01)

(58) Field of Classification Search
CPC ... A61B 5/4585; A61B 5/1121; A61B 5/1126; A61B 5/702
See application file for complete search history.

(56) References Cited

U.S. PATENT DOCUMENTS 4,534,364 A    8/1985  Lamoreux
4,583,554 A    4/1986  Mittelman
(Continued)

FOREIGN PATENT DOCUMENTS

| CA | 1225150 | 8/1987 |
|---|---|---|
| WO | 2008040790 | 4/2008 |
| WO | 2012143628 | 10/2012 |

OTHER PUBLICATIONS

United States Patent and Trademark Office (USPTO), International Search Report and Written Opinion, dated Mar. 13, 2015, related PCT international application No. PCT/US2014/070936, pp. 1-9, claims searched, pp. 10-15.
(Continued)

*Primary Examiner* — Daniel L Cerioni
(74) *Attorney, Agent, or Firm* — O'Banion & Ritchey LLP; John P. O'Banion (57) ABSTRACT

Devices and methods are disclosed for quantifying temporal changes in human anterior cruciate ligament (ACL) structural properties, such as Anterior-Posterior tibial shear force (TSF) and Anterior-Posterior tibial shear displacement (TSD) for testing ACL overuse injury during training and minimizing or preventing ACL injury.

14 Claims, 4 Drawing Sheets

Related U.S. Application Data continuation of application No. PCT/US2014/070936, filed on Dec. 17, 2014.

(60) Provisional application No. 61/916,927, filed on Dec. 17, 2013.

(51) Int. Cl.
    *A61B 5/296*  (2021.01)
    *A61B 5/389*  (2021.01)

(56) References Cited

U.S. PATENT DOCUMENTS

| | | |
|---|---|---|
| 4,913,163 A | 4/1990 | Roger |
| 5,662,121 A | 9/1997 | Zucker |
| 8,444,564 B2 | 5/2013 | Mahfouz |
| 2011/0071534 A1 | 3/2011 | Tuke |
| 2012/0046540 A1 | 2/2012 | Branch |
| 2012/0226199 A1 | 9/2012 | Nouveau |
| 2014/0342623 A1 | 11/2014 | Gates |
| 2015/0032030 A1 | 1/2015 | Iglesias |

OTHER PUBLICATIONS

Starkel, Cambrie D. et al., "investigation of the Temporal Response of Anterior Knee Laxity Following Strenuous Exercise", University of California, Davis, Davis, California, poster presentation, prensented at the 2014 American College of Sports Medicine (ACSM) conference held in Orlando, Florida, May 27-31, 2014.

DIAGNOSTIC KNEE ARTHROMETER FOR DETECTING ACL STRUCTURAL CHANGES

CROSS-REFERENCE TO RELATED APPLICATIONS

This application is a continuation of U.S. patent application Ser. No. 15/177,033 filed on Jun. 8, 2016, incorporated herein by reference in its entirety, which is a 35 U.S.C. § 111(a) continuation of PCT international application number PCT/US2014/070936 filed on Dec. 17, 2014, incorporated herein by reference in its entirety, which claims priority to, and the benefit of, U.S. provisional patent application Ser. No. 61/916,927 filed on Dec. 17, 2013, incorporated herein by reference in its entirety. Priority is claimed to each of the foregoing applications.

The above-referenced PCT international application was published as PCT International Publication No. WO 2015/095383 on Jun. 25, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to injury prevention systems and methods, and more particularly to systems and methods for prevention of, or minimizing the occurrence of, injuries to the anterior cruciate ligament (ACL).

2. Background Discussion

Injury to the knee, and specifically the anterior cruciate ligament (ACL) within the knee, is one of the most common and debilitating sports related injuries. ACL injuries are an important clinical problem, and there is a need for more effective injury prevention approaches. ACL injury is reported as the most frequent and severe ligamentous injury to the knee. It has been estimated that between 80,000 and 250,000 ACL injuries occur annually within the United States. The annual cost to treat ACL injuries has been estimated at between one and two billion dollars. Women have a 2 to 10 times greater ACL injury incidence rate compared to men. Young athletes are especially vulnerable, with approximately 50% of ACL injuries occurring in the 15 to 25 year old population. Approximately 70-80 percent of ACL injuries are non-contact in nature and often the injury occurs during a movement that the person has performed many times before without incidence, suggesting an overuse injury mechanism.

The primary ACL injury prevention intervention strategy is to develop training programs that target specific factors that an athlete can modify to reduce ACL loading during movement (e.g. muscle strength, coordination and movement mechanics). The limitations of existing devices include: (1) inability to quantify a continuous force-deformation profile, many devices only measure displacement for a fixed force, (2) inability to ensure a relaxed muscle state, (3) inability to separate soft tissue deformation from actual bone displacement, (4) the potential for joint contact forces to contribute resistance to tibial translation, and (5) the weight of the limb segment and device applying a tibial shear force.

An object of the present disclosure is a knee arthrometer that overcomes one or more of the above-described limitations.

BRIEF SUMMARY

The present description details a device and methodology to quantify changes in a person's ACL structural properties over time. Beneficially, the device can: (1) test either knee, (2) position the knee flexion angle at a preferred range between approximately 25 and approximately 30 degrees, as well as other ranges between 0 and 90 degrees, (3) place a small traction force on the lower leg to reduce tibia-meniscii-femur contact forces, (4) induce a smooth continuous anterior-posterior (A-P) translational of the tibia relative to the femur, (5) accurately record tibial shear force and the displacement of the tibia relative to the femur, and (6) monitor muscle activation to ensure non-active muscles during testing.

In one aspect, the arthrometer of the present description comprises a testing frame, two force transducers, two string potentiometers, two sets of skin electrodes, a processing device (e.g. computer) with analog-to-digital interface, and custom application software for processing acquired data from the instrument.

In one embodiment, the arthrometer includes: (1) real time, continuous, force-deformation, display and recording, (2) electromyography to ensure relaxed muscles during testing, (3) direct measurement of the relative location of femur and tibial tuberosity to eliminate displacement errors that can result from soft tissue deformation that is not accounted for with many devices, (4) vertical orientation of the leg during testing to: (a) apply a traction force at the knee to eliminate bone-cartilage contact forces contributing resistance to tibial shear displacement, and (b) prevent the weight of the leg and testing device from applying a tibial shear force.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

FIG. 1 through FIG. 4B show a system and method, and testing relating to the same, for prevention of, or minimizing the occurrence of, injuries to the anterior cruciate ligament (ACL). The systems and methods disclosed herein are premised around an injury prevention intervention strategy utilizing training programs that target specific factors that an athlete can modify to reduce ACL loading during movement (e.g. muscle strength, coordination and movement mechanics).

One basic premise of the present description is that many non-contact ACL injuries result from an overuse mechanism (i.e. repeated loading of and subsequent mechanical breakdown of the ligament and damage accumulation).

Another premise of the present description is that accumulated ACL damage can be detected, particularly using a knee arthrometer as provided in further detail below.

A further premise is that a more effective ACL injury prevention program will incorporate regular monitoring of knee laxity. Training programs that promote strength and movement mechanics that reduce the stress and strain imposed on the ACL during individual loading cycles can be beneficial, but if the training programs involve loading frequencies, durations or rates that cause damage without sufficient recovery time, then the training programs themselves may contribute to ACL injury. One important potential mechanism of non-contact ACL injury is overuse, defined as the repeated loading of a ligament and the subsequent mechanical breakdown of the ligament characterized by a change in the ligament's biomechanical properties such as ultimate force and stiffness. Changes in knee ligament biomechanical properties are reflected in knee laxity changes. It is proposed that overuse mechanisms contribute to many non-contact ACL injuries and knee laxity monitoring, as disclosed herein, provides an opportunity to detect overuse injuries before they result in catastrophic ACL rupture.

It is also proposed that knee laxity changes consistent with knee structural damage accumulation can occur following strenuous exercise. The systems and methods of the present disclosure detail a knee arthrometer capable of accurately quantifying, within minutes, knee anterior-posterior (A-P) force-deformation (F-d) behavior and specifically knee laxity (i.e. the relative displacement of the tibia relative to the femur when subjected to a specific force). One application of this device is to: (1) quantify the normal temporal response of knee F-d behavior to strenuous physical activity, (2) provide evidence (i.e. knee laxity changes) that knee structures may become compromised during strenuous activity.

Figure 1:
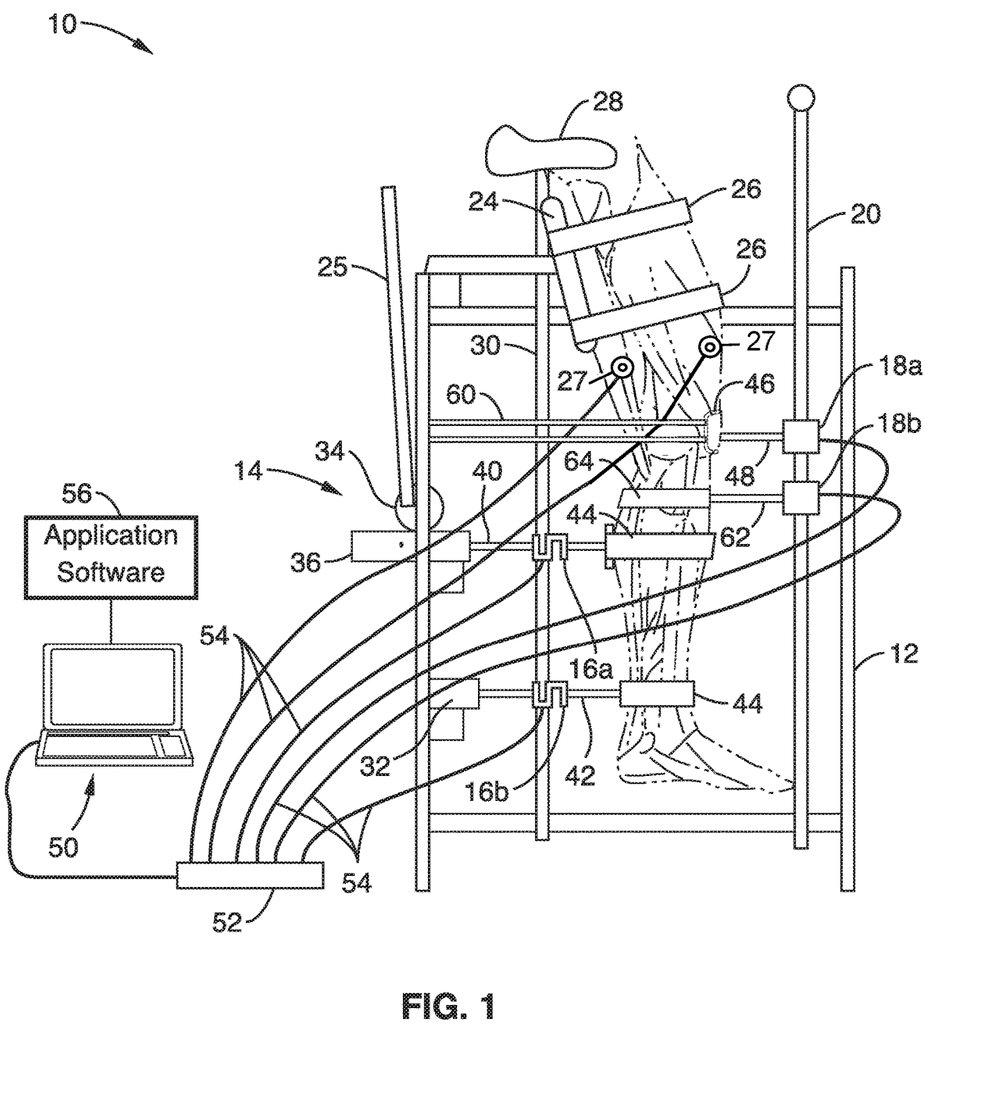
FIG. 1 is a schematic diagram showing a side view of the knee arthrometer of the present description.

FIG. 1 is a schematic diagram showing a side view of the knee arthrometer 10 comprising an instrumented custom tibial shear force applicator 14 in accordance with the present description. Knee arthrometer apparatus 10 preferably includes an upper leg/thigh support (stabilizer) 24 with one or more electrodes 27 for monitoring quadriceps and hamstrings muscle activation, a pair of string potentiometers 18a and 18b to quantify the A-P location of the tibia relative to the femur, a manual force actuator 25 for applying A-P tibial translation, and a pair of force transducers 16a and 16b configured to determine tibial shear force (TSF). The signals from string potentiometers 18a and 18b and force transducers 16a and 16b are recorded and displayed in real-time using, for example, a laptop computer 50 and application software 56. String potentiometers 18a and 18b and force transducers 16a and 16b signals are shown in FIG. 1 to be coupled to computer via a series of leads 54 and analog to digital (A-D) interface 52. However, it is appreciated that string potentiometers 18a and 18b and force transducers 16a and 16b signals may also be coupled to computer 50 or analog to digital interface 52 via wireless means, e.g. IR, Wi-Fi, Bluetooth or other wireless couplings available in the art.

As illustrated in FIG. 1, an embodiment of the knee arthrometer apparatus 10 according to the present disclosure includes two force transducers 16a and 16b, (e.g. LC101-100 S Beam Load Cell, Omega Inc, Stamford, Conn.), two high precision string potentiometers 18a, 18b (e.g. SP1-4 String Pot, Celesco, Chatsworth, Calif.), and two sets of skin electrodes 27. It is appreciated that other configurations of potentiometers and electrodes may also be incorporated as appropriate.

Knee arthrometer apparatus 10 also includes a support frame 12 that acts as the foundation measurement instrumentation and for attachment to the patient's anatomy. The support frame 12 houses tibial shear force applicator 14 that comprises a manual force applicator 25 coupled to a rack 36-and-pinion 34 driven force applicator. In an alternative embodiment, an electronic actuator and safety stops (not shown) may be used in place of the manual applicator.

The support frame 12 also supports a bicycle style seat 28 (via post 30) and handle bars 20 to provide a familiar body support system for most subjects. The seat 28 supports the person's body weight. The handle bars 20 provide support as a person mounts and dismounts the bicycle seat 28. The subject sits on the seat 28 and grips the handle bars 20 as needed for additional support.

A thigh support 24 is adjusted from below and behind the seat 28 to support the thigh and to secure it in an optimal position between approximately 25 and approximately 30 degrees relative to the vertical (other orientations are contemplated). Two bindings 26 (which may comprise quick-release ratcheting bindings available in the art) are used to secure the thigh to the thigh support 24 and provide stabilization to the upper leg. The lower leg ideally hangs parallel with the vertical. The tibial shear force applicator 14 (i.e., lower leg rack-and-pinion force actuator) with a first (upper) force transducer 16a is secured to the lower leg just below the tibial tuberosity (proximal third of lower leg) via a cuff 44 (which may comprise a padded support and a Velcro strap) and coupling 40. The ankle is restrained from Anterior-Posterior (A-P) motion with a cuff 44 and coupling 42 equipped with a second (lower) force transducer 16b to quantify the restraining force. Adjustable attachment means 32 may be used to adjustably secure (e.g. via extension toward or away from the user's ankle) the coupling 42 to the support frame 12. A bar (not shown) may also be used to limit the subject's foot from internal/external rotation during testing.

The two string potentiometers 18a and 18b are preferably positioned substantially perpendicular to the lower leg in the A-P direction, with a first upper potentiometer 18a held directly over the patella and secured to the femur via an oval ring 46 surrounding the patella. The ring 46 may comprise a small tube is bent to fit around the patella, and is held firmly against the skin covering the femur via one or more straps 60 pulled tight and secured to the support frame 12. A string or like coupling 48 is secured to both sides of the ring 46 and given sufficient length to extend out away from the knee without touching the skin over the patella connecting the medial and lateral sides of the patella ring. The upper string potentiometer 18a connects to this coupling 48.

The lower potentiometer 18b is secured to the skin covering the tibial tuberosity using Velcro straps 64 wrapped around the leg and string coupling 62.

While the configuration shown in FIG. 1 is preferred, it is appreciated that other orientations and/or variations of the components of knee arthrometer apparatus 10 may be employed. For example, the lower force transducer 16b and coupling 42 could be located in front rather that behind the leg. The electrode pads 27 may also be placed over different muscles if desired. Furthermore, other sensors for the displacement measurements (e.g. lasers, ultrasound, etc.) may be used in place of string potentiometers 18a and 18b.

Knee arthrometer apparatus 10 further includes a laptop computer 50 with an analog to digital interface 52, and application software 56 running on the computer 50 to receive data from electrode pads 27, transducers 16a and 16b and potentiometers 18a and 18b. Electrode pads 27 are placed on the subject's skin over the thigh quadriceps and hamstrings muscles to monitor quadriceps and hamstrings muscle activity.

Figure 2:
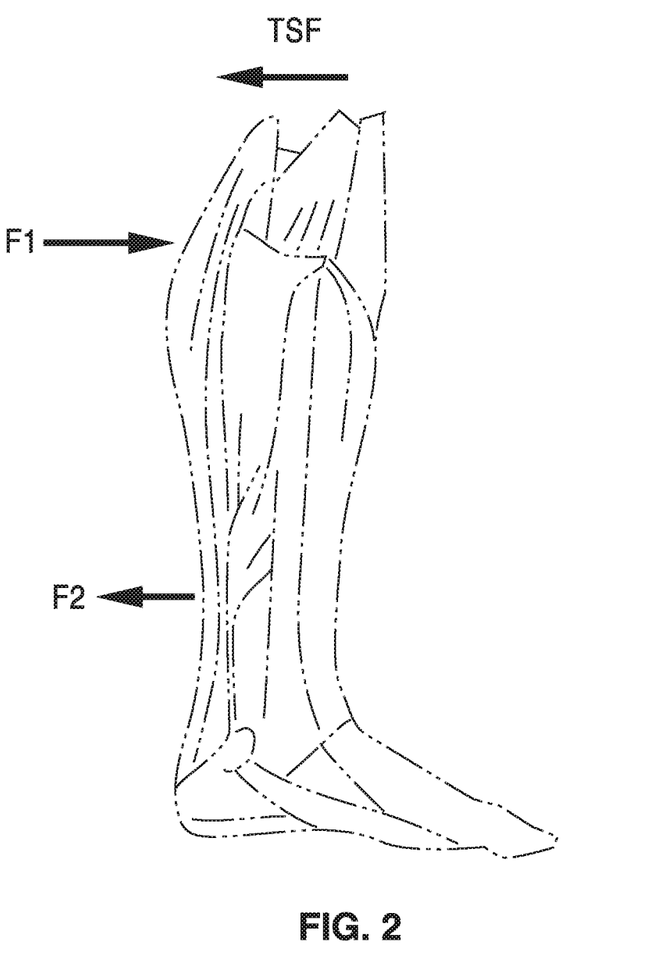
FIG. 2 is a schematic diagram illustrating the forces acting on the lower leg in the anterior-posterior (A-P) direction.

FIG. 2 schematically illustrates the forces acting on the lower leg in the A-P direction. The tibial shear force (TSF), which is primarily provided by the ACL during anterior displacement and the posterior cruciate ligament during posterior displacement, is equal to the difference in the force applied by the actuator (F1) and the ankle restraining force (F2).

The Anterior-Posterior tibial shear force (TSF) (FIG. 2) is calculated from the difference in the two force transducer 16a and 16b forces. The A-P tibial shear displacement (TSD) is calculated from the difference in the string potentiometer 18a, 18b location measurements. ACL force and displacement are estimated from TSF and TSD (see also FIG. 2).

It is preferred that certain leg muscles (e.g. hamstrings, quadriceps) are not active during a laxity test because such muscle activity can alter the acquired laxity reading. Application software 56 is preferably configured to acquire data from the electrode pads 27 and display the electrical activity of these muscles during a test. If these signals are above a designated threshold, then that trial is discarded and the test repeated.

The knee arthrometer apparatus 10 provides for: (1) real time, continuous, force-deformation, display and recording, (2) muscle activity feedback to ensure that laxity measurements are only determined when muscles are quiescent, (3) direct measurement of the relative location of femur and tibia to eliminate displacement errors that can result from soft tissue deformation that is not accounted for with many devices, (4) vertical orientation of the leg during testing to: (a) apply a traction force at the knee to eliminate bone-cartilage contact forces contributing resistance to tibial shear displacement, and (b) prevent the weight of the leg and testing device from applying a tibial shear force.

Studies were conducted to validate the efficacy and function of the knee arthrometer of the present description. Several examples follow that document the results from these studies.

Example 1

Measuring the anterior displacement of the tibia relative to the femur can be problematic due to how devices are attached to the body and forces applied, but the novel attachment system of knee arthrometer apparatus 10 eliminates many of these problems. It was found that the key to an accurate measurement was to provide a relatively constant force against the bone where the displacement measurements are made. The string potentiometers 18a, 18b provide a relatively constant retraction force. The force at the attachment location of potentiometer 18b (FIG. 1) remains relatively constant during any displacement of the lower leg, therefore giving reliable measures.

Tracking the displacement of the femur is more difficult. In a preferred configuration, patella loops were used that could encapsulate the patella, but be secured to the femur. It was found the attachment means of potentiometer 18a (FIG. 1) provides a relatively constant force on the femur that does not change during testing, thus eliminating measurement errors created by other methods that can cause variable soft tissue deformation during the test.

Several steps were taken to test the validity and utility of using the knee arthrometer to obtain accurate Force-deformation (F-d) behavior of the knee. First, the force transducers 16a and 16b and string potentiometers 18a and 18b selected for use in the knee arthrometer apparatus 10 were calibrated and their resolution, accuracy, and precision evaluated relative to our measurement needs. The calibration was performed multiple times across a series of days to characterize the resolution, accuracy, and precision of the sensors and the day-to-day variations in these measures. Resolution defines the smallest signal difference that the instrumentation can detect. Accuracy is a measure of how closely the instrumentation system can estimate the true signal. Precision is a measure of how well an instrumentation system reproduces the same output for a given input when measured on different occasions. Force transducers 16a and 16b were calibrated over a 0-350 N range. String potentiometers 18a and 18b were calibrated over a range of 0-120 mm in 10 mm increments. All instruments demonstrated excellent linearity with $R^2$ values from the calibrations being 1.0. The instrumentation was stable, having an average percent difference between calibrations performed on different days and times of day of less than 0.22% for the force transducers 16a and 16b and 0.7% for the string potentiometers 18a and 18b. The force transducer had an average accuracy better than 0.62 N or 0.14% full scale operation (FSO=445 N), an average precision better than 0.16 N or 0.03% FSO and an average resolution better than 0.60 N or 0.13% FSO.

It was determined that the knee arthrometer apparatus 10 of the present description is capable of detecting a change in laxity of equal to or less than 1 mm. The string potentiometers 18a and 18b had an average accuracy of better than 0.43 mm or 0.36% FSO (FSO=120.65 mm), an average precision of better than 0.14 mm or 0.12% FSO, and an average resolution of better than 0.20 mm or 0.17% FSO. From these data, the string potentiometers were deemed acceptable for the knee arthrometer application.

Example 2

Figure 3A:
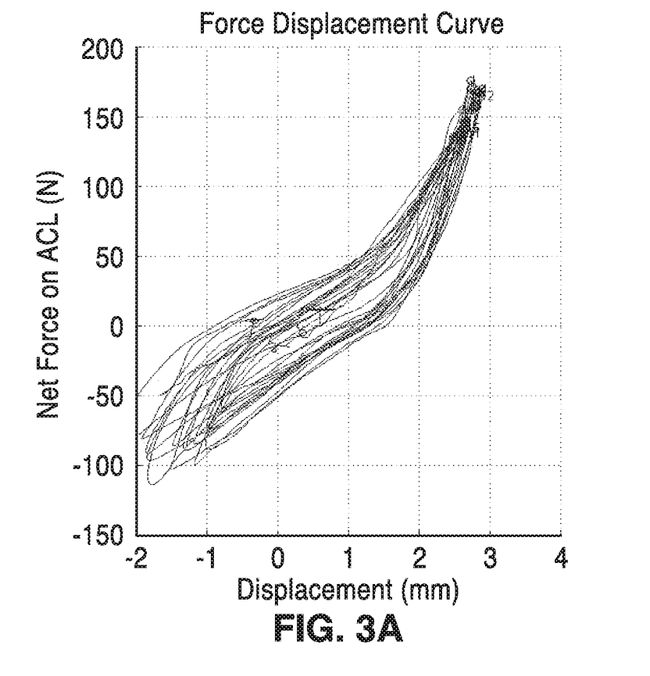
FIG. 3A and FIG. 3B show the estimated ACL force deformation profile during approximately 20 anterior-posterior loading cycles for a subject tested at two different times.
Figure 3B:
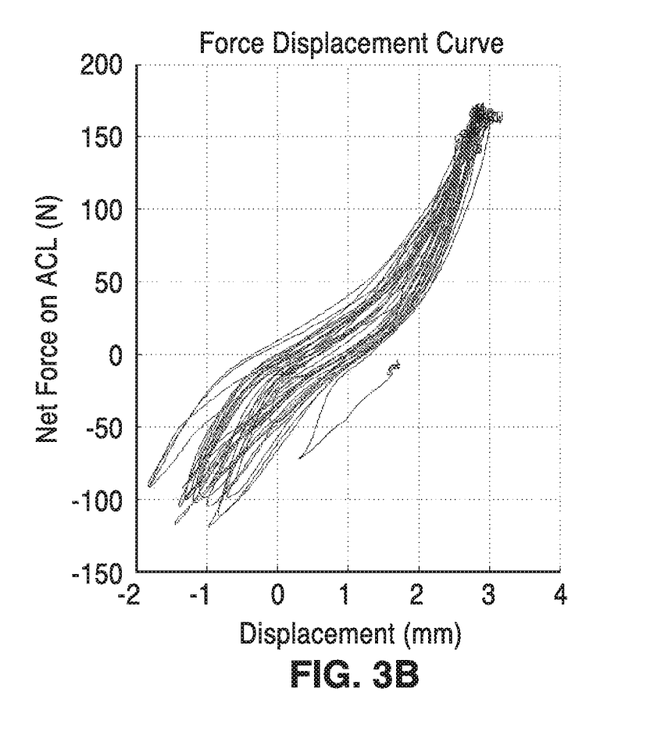

We next tested the repeatability of the knee arthrometer apparatus 10 for making knee laxity measurements. Fifteen subjects were tested hourly for five hours and allowed only to work at a computer and take short walking breaks. Right knee laxity was determined each hour. ACL force-deformation curves resulting from two tests separated by an hour are illustrated in FIG. 3A and FIG. 3B, respectively. FIG. 3A and FIG. 3B show the estimated ACL force deformation profile during ~20 anterior-posterior loading cycles for a subject tested at two different times. Similar profiles were obtained for each test. The average knee laxity within each subject varied by less than 0.5 mm and showed no trend. The above results confirm that the knee arthrometer apparatus 10 of the present description can reliably measure knee laxity to within 0.5 mm.

Example 3

The knee arthrometer apparatus 10 was also used to acquire preliminary data pertaining to the specific theory that repeated bouts of strenuous exercise can lead to laxity changes in the knee, reflective of structural alterations (i.e. damage) in the ACL. Before presenting results from these tests, a brief description of the rationale supporting overuse mechanisms of catastrophic ACL injury is warranted.

The basic mechanisms of ACL injuries incurred during non-contact movement that a person has performed many times previously without incident are not understood, but there is evidence supporting overuse mechanisms, e.g. that micro-trauma, or selective fiber disruption, of the human ACL may be caused by a rapid increase in training load, frequency, and/or duration. A ligament may be able to heal certain levels of micro-damage if given sufficient recovery time. However, if strenuous activity occurs at a frequency that creates micro-damage faster than it can be repaired by the healing process, then micro-damage accumulates compromising the structural integrity of the ligament. Given this situation, an ACL may rupture when subjected to forces created during movements routinely performed by the individual without injury in the past. This response is consistent with many non-contact ACL injuries observed in sports.

The knee arthrometer apparatus 10 provides a platform to investigate overuse mechanisms of ACL injury. A premise of the technology is that strenuous, repetitive exercise causes a change in knee laxity that will return to pre-exercise levels within hours following the exercise in some individuals (those people experiencing only the viscoelastic response), but not others (those experiencing both the viscoelastic response coupled with ligament micro-damage). Those people who show full recovery within 5 hours likely experienced dynamic creep in their ACL, while those who do not fully recovery within 5 or 24 hours, likely experienced dynamic creep plus some ACL micro-damage. It follows that a chronic change in knee laxity can be used as an indicator of ACL structural damage.

Example 4

Figure 4A:
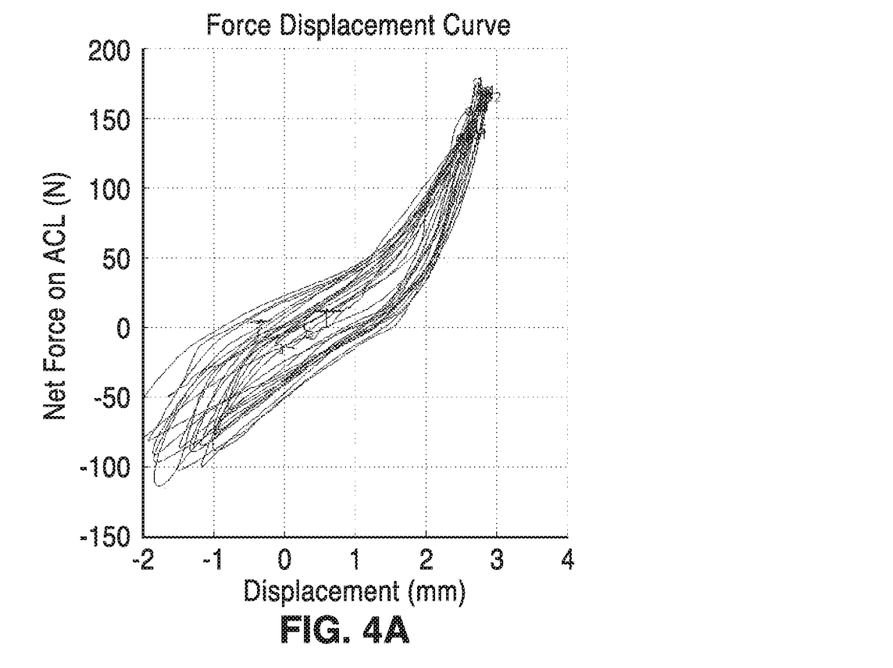
FIG. 4A and FIG. 4B show plots illustrating the estimated ACL force-deformation profile during approximately 20 anterior-posterior loading cycles prior to exercise (FIG. 4A) and following exercise (FIG. 4B).
Figure 4B:
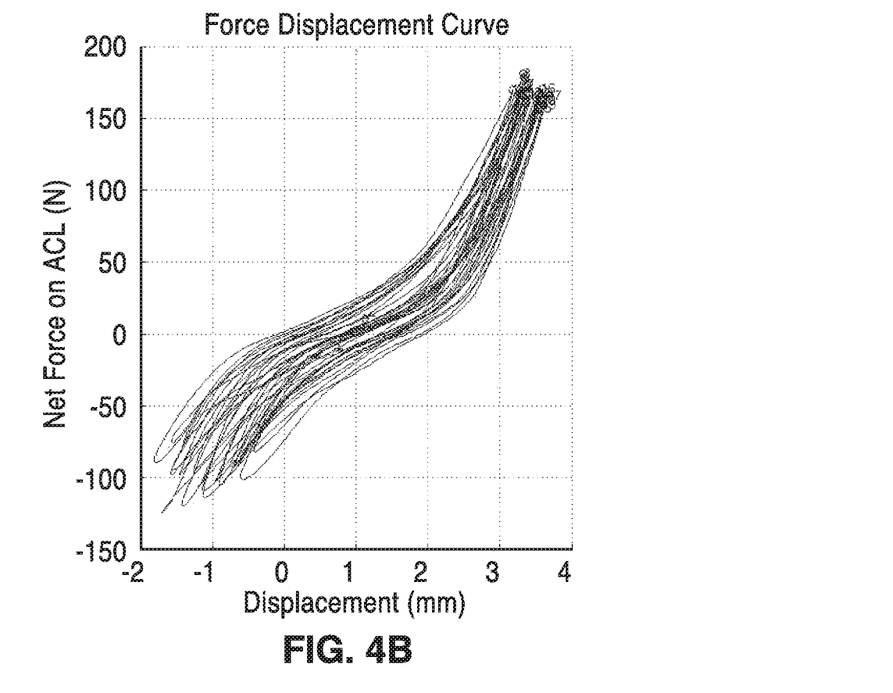

Results from preliminary work using our knee arthrometer provide evidence that some people may sustain ACL micro-trauma following strenuous exercise. It was found that knee laxity in individuals completing a rigorous 50 minute strength and agility exercise protocol increased by 0.5 mm to 2 mm compared to the pre-exercise condition, recovered to pre-exercise levels in 1 to 5 hours for most people, but not everyone. FIG. 4A and FIG. 4B show plots illustrating the estimated ACL force-deformation profile during ~20 anterior-posterior loading cycles prior to exercise (FIG. 4A) and following exercise (FIG. 4B). This person experienced an average increased knee laxity of approximately 0.6 mm as a result of the exercise. Several people maintained laxity changes 24 hours post-exercise and did not recover to pre-exercise laxity values for several days.

In summary, a prototype knee arthrometer was developed and used to quantify knee anterior-posterior (A-P) force-deformation (F-d) behavior in young adults pre- and post-strenuous exercise. The results support the theory that subtle damage to knee structures can result from strenuous exercise in some people and that the knee arthrometer can detect these changes.

Computer program instructions described in application software of the present description, such as embodied in computer-readable program code logic, may be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that the present disclosure encompasses multiple embodiments which include, but are not limited to, the following:

1. An apparatus for measuring one or more physiological characteristics of a subject's knee, comprising: a support frame configured for stabilizing an upper leg of the subject; one or more force transducers configured to couple to the support frame and the lower leg of the subject; one or more potentiometers configured to couple to the support frame and leg of the subject; one or more electrodes configured to be coupled to the subject's skin; a tibial shear force applicator coupled to the support frame and the lower leg of the subject; a processor; and programming executable on the processor for analyzing one or more signals from the one or more transducers, potentiometers and skin electrodes.

2. The apparatus of any preceding embodiment, wherein the one or more potentiometers comprise a pair of string potentiometers positioned substantially perpendicular to the lower leg in the (A-P) direction.

3. The apparatus of any preceding embodiment, wherein the tibial shear force applicator comprises a manual force applicator comprising a rack and pinion.

4. The apparatus of any preceding embodiment, wherein the tibial shear force applicator is positioned on the support frame for attachment via a coupling to the lower leg at a location below a tibial tuberosity of the lower leg.

5. The apparatus of any preceding embodiment, wherein the one or more force transducers comprises a first force transducer coupled to the tibial shear force applicator and a second force transducer coupled to the subject at a location at or near an ankle of the subject.

6. The apparatus of any preceding embodiment, further comprising a cuff coupled to the support frame, said cuff configured to be secured to said location at or near the ankle such that the ankle is substantially restrained from Anterior-Posterior (A-P) motion.

7. The apparatus of any preceding embodiment, wherein the second force transducer is coupled to the cuff to quantify a force associated with said A-P motion restraint.

8. The apparatus of any preceding embodiment, wherein the pair of string potentiometers comprises an upper string potentiometer attached at a location of the support frame configured to allow the upper string potentiometer to be coupled to the subject at a patella of the subject's leg.

9. The apparatus of any preceding embodiment, wherein the upper string potentiometer is secured to the patella via an oval ring surrounding the patella.

10. The apparatus of any preceding embodiment, wherein the pair of string potentiometers comprises a lower string potentiometer attached at a location of the support frame configured to allow the lower string potentiometer to be coupled to the subject at or near a tibial tuberosity of the lower leg.

11. The apparatus of any preceding embodiment, wherein the programming is configured for calculating an Anterior-Posterior tibial shear force (TSF) as a function of a difference between the signals from the first force transducer and the second force transducer.

12. The apparatus of any preceding embodiment, wherein the programming is configured for calculating an Anterior-Posterior tibial shear displacement (TSD) as a function of a difference between location measurements of the pair of string potentiometers.

13. The apparatus of any preceding embodiment, further comprising: wherein the support frame is configured for stabilizing the upper leg of a subject via a thigh support configured to support the thigh and to secure it in a position between approximately 25 and approximately 30 degrees relative to vertical.

14. The apparatus of any preceding embodiment, further comprising a seat and handlebars coupled to the support frame for supporting the subject.

15. A knee arthrometer apparatus for measuring one or more physiological characteristics of a subject's knee, comprising: a support frame configured for stabilizing an upper leg of the subject; one or more force transducers configured to couple to the support frame and lower leg of the subject; one or more potentiometers configured to couple to the support frame and leg of the subject; one or more electrodes configured to be coupled to the subject's skin; a tibial shear force applicator coupled to the support frame and lower leg of the subject; a processor; and programming executable on the processor for analyzing one or more signals from the one or more transducers, potentiometers and skin electrodes to calculate one or more of anterior cruciate ligament (ACL) force or displacement.

16. The apparatus of any preceding embodiment, wherein the one or more potentiometers comprise a pair of string potentiometers positioned substantially perpendicular to the lower leg in the (A-P) direction.

17. The apparatus of any preceding embodiment, wherein the tibial shear force applicator comprises a manual force applicator comprising a rack and pinion.

18. The apparatus of any preceding embodiment, wherein the tibial shear force applicator is positioned on the support frame for attachment via a coupling to the lower leg at a location below a tibial tuberosity of the lower leg.

19. The apparatus of any preceding embodiment, wherein the one or more force transducers comprises a first force transducer coupled to the tibial shear force applicator and a second force transducer coupled to the subject at a location at or near an ankle of the subject.

20. The apparatus of any preceding embodiment, further comprising a cuff coupled to the support frame, said cuff configured to be secured to said location at or near the ankle such that the ankle is substantially restrained from Anterior-Posterior (A-P) motion.

21. The apparatus of any preceding embodiment, wherein the second force transducer is coupled to the cuff to quantify a force associated with said A-P motion restraint.

22. The apparatus of any preceding embodiment, wherein the pair of string potentiometers comprises an upper string potentiometer attached at a location of the support frame configured to allow the upper string potentiometer to be coupled to the subject at a patella of the subject's leg.

23. The apparatus of any preceding embodiment, wherein the upper string potentiometer is secured to the patella via an oval ring surrounding the patella.

24. The apparatus of any preceding embodiment, wherein the pair of string potentiometers comprises a lower string potentiometer attached at a location of the support frame configured to allow the lower string potentiometer to be coupled to the subject at or near a tibial tuberosity of the lower leg.

25. The apparatus of any preceding embodiment, wherein the programming is configured for calculating an Anterior-Posterior tibial shear force (TSF) as a function of a difference between the signals from the first force transducer and the second force transducer.

26. The apparatus of any preceding embodiment, wherein the programming is configured for calculating an Anterior-Posterior tibial shear displacement (TSD) as a function of a difference between location measurements of the pair of string potentiometers.

27. The apparatus of any preceding embodiment, further comprising: wherein the support frame is configured for stabilizing the upper leg of a subject via a thigh support configured to support the thigh and to secure it in a position between approximately 25 and approximately 30 degrees relative to vertical.

28. A method for measuring one or more physiological characteristics of a subject's knee, comprising: stabilizing an upper leg of the subject; coupling one or more force transducers configured to couple to a lower leg region of the subject; coupling one or more potentiometers configured to the leg of the subject; coupling one or more electrodes to the subject's skin; applying a tibial shear force to the lower leg of the subject; and analyzing one or more signals from the one or more transducers, potentiometers and skin electrodes to calculate one or more of anterior cruciate ACL force and displacement 29. The method of any preceding embodiment, wherein the one or more potentiometers comprise a pair of string potentiometers positioned substantially perpendicular to the lower leg in the (A-P) direction.

30. The method of any preceding embodiment, wherein the tibial shear force is applied to the lower leg at a location below a tibial tuberosity of the lower leg.

31. The method of any preceding embodiment, wherein the one or more force transducers comprises a first force transducer coupled to the application of the tibial shear force and a second force transducer coupled to the subject at a location at or near an ankle of the subject.

32. The method of any preceding embodiment, further comprising: restraining the lower leg at or near the ankle such that the ankle is substantially restrained from Anterior-Posterior (A-P) motion.

33. The method of any preceding embodiment, wherein the pair of string potentiometers comprises an upper string potentiometer attached at a patella of the subject's leg and a lower string potentiometer attached at or near a tibial tuberosity of the lower leg.

34. The method of any preceding embodiment, further comprising: calculating an Anterior-Posterior tibial shear force (TSF) as a function of a difference between the signals from the first force transducer and the second force transducer.

35. The method of any preceding embodiment, further comprising: calculating an Anterior-Posterior tibial shear displacement (TSD) as a function of a difference between location measurements of the pair of string potentiometers.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for measuring one or more physiological characteristics of a subject's knee, comprising:
   a support frame configured for stabilizing an upper leg of the subject;
   one or more force transducers configured to couple to the support frame and lower leg of the subject;
   one or more displacement measurement sensors disposed in relation to the support frame and leg of the subject;
   one or more electrodes configured to be coupled to the subject;
   a tibial shear force applicator coupled to the support frame and the lower leg of the subject;
   a processor; and
   programming executable on the processor for analyzing one or more force transducer, displacement measurement sensor and/or electrode signals;
   wherein the tibial shear force applicator is positioned on the support frame configured for attachment via a coupling to the lower leg at a location below a tibial tuberosity of the lower leg;
   wherein the one or more force transducers comprises a first force transducer coupled to the tibial shear force applicator and a second force transducer configured to be coupled to the subject at a location at or near an ankle of the subject; and
   wherein the programming is configured for calculating an Anterior-Posterior (A-P) tibial shear force (TSF) as a function of a difference between signals from the first force transducer and signals from the second force transducer.

2. The apparatus of claim 1, wherein the one or more displacement measurement sensors comprise a pair of string potentiometers positioned perpendicularly to the lower leg in the (A-P) direction.

3. The apparatus of claim 1, wherein the tibial shear force applicator comprises a manual force applicator comprising a rack and pinion.

4. The apparatus of claim 1, wherein the one or more displacement measurement sensors comprise an ultrasound or laser-based measuring device.

5. The apparatus of claim 1, further comprising a cuff coupled to the support frame, said cuff configured to be secured to said location at or near an ankle such that the ankle is restrained from Anterior-Posterior (A-P) motion.

6. The apparatus of claim 5, wherein the cuff is further coupled to the second force transducer configured to quantify a force associated with A-P motion restraint.

7. The apparatus of claim 2, wherein the pair of string potentiometers comprises an upper string potentiometer attached at a location of the support frame configured to allow the upper string potentiometer to be coupled to the subject at a patella of the subject's leg.

8. The apparatus of claim 7, wherein the upper string potentiometer is configured to be secured to the patella via an oval ring surrounding the patella.

9. The apparatus of claim 2, wherein the pair of string potentiometers comprises a lower string potentiometer attached at a location of the support frame configured to allow the lower string potentiometer to be coupled to the subject at or near a tibial tuberosity of the lower leg.

10. The apparatus of claim 2, wherein the programming is configured for calculating an Anterior-Posterior tibial shear displacement (TSD) as a function of a difference between location measurements of the pair of string potentiometers.

11. The apparatus of claim 1, further comprising:
   wherein the support frame is configured for stabilizing the upper leg of a subject via a thigh support configured to support the thigh and to secure it in a position between approximately 25 and approximately 30 degrees relative to vertical.

12. The apparatus of claim 1, further comprising:
   a seat and handlebars coupled to the support frame for supporting the subject.

13. The apparatus of claim 1:
   wherein the programming executable on the processor is configured to calculate one or more of anterior cruciate ligament (ACL) force or displacement from the one or more signals.

14. The apparatus of claim 1, wherein the programming is further configured to calculate an A-P tibial shear displacement (TSD) from displacement measurement sensor signals.

* * * * *